US006353131B1

(12) United States Patent
Beckmann et al.

(10) Patent No.: US 6,353,131 B1
(45) Date of Patent: Mar. 5, 2002

(54) COMPOSITION CONTAINING AT LEAST ONE SULFINIC DERIVATIVE AND POTASSIUM CARBONATE

(75) Inventors: Eberhard Beckmann, Neustadt; Rudolf Krüger, Weisenheim, both of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/525,061

(22) Filed: Mar. 14, 2000

(30) Foreign Application Priority Data

Mar. 15, 1999 (DE) .......................................... 199 11 357

(51) Int. Cl.$^7$ ............................................ C07C 309/00
(52) U.S. Cl. ........................ 562/125; 562/126; 252/22; 252/188
(58) Field of Search ................................ 562/125, 126; 252/188, 21; 560/150; 258/21

(56) References Cited

U.S. PATENT DOCUMENTS

| 3,054,658 A | 9/1962 | Franklin et al. | ............... 23/116 |
| 3,677,699 A | 7/1972 | Fujiwara et al. | ............... 23/116 |
| 3,819,807 A | 6/1974 | Schreiner et al. | ........... 423/265 |
| 4,676,961 A | * 6/1987 | Appl et al. | |
| 5,296,210 A | 3/1994 | Oglesby | ..................... 423/275 |

FOREIGN PATENT DOCUMENTS

| DE | A 199 05 395 | | 2/1999 |
| JP | A 1970/26 610 | | 9/1970 |
| JP | 51-110497 | * | 3/1975 |
| JP | 51 110497 | | 9/1976 |
| JP | 51 110 497 | | 9/1976 |
| JP | 52 015556 | | 4/1997 |
| SU | 1 143 786 | | 3/1985 |
| SU | 1143786 | * | 3/1985 |

* cited by examiner

*Primary Examiner*—Gary Geist
*Assistant Examiner*—Hector M Reyes
(74) *Attorney, Agent, or Firm*—Keil & Weinkauf

(57) ABSTRACT

Sulfinic derivatives such as zinc dithionite, sodium dithionite, zinc or sodium hydroxymethyl sulfinate or zinc or sodium hydroxy-ethyl sulfinate, their condensation products with ammonia, and aminoiminomethanesulfinic acid are stabilized to degradation by admixture of potassium carbonate.

7 Claims, No Drawings

COMPOSITION CONTAINING AT LEAST ONE SULFINIC DERIVATIVE AND POTASSIUM CARBONATE

The present invention relates to compositions containing sulfinic derivatives. In particular it relates to such compositions as contain sulfinic derivatives having reductive properties and in which the sulfinic derivative is stabilized to degradation by the addition of stabilizing agents.

Sulfinic derivatives are derivatives of sulfinic acid of the general formula

R—S(O)—O$^-$M$^+$.

The substituent R denotes an organic radical, such as a substituted or unsubstituted alkyl or aryl radical, or an inorganic radical, such as a substituted or unsubstituted sulfino or sulfinato radical. The substituent M$^+$ stands for a cation such as a proton, a unipositively charged metal cation or the equivalent of a multipositively charged metal cation necessary to compensate the electric charges.

Sulfinic derivatives have reductive properties and are industrially important auxiliaries primarily in the textile and paper industries, for example for the reduction of dyes in vat dyeing or for bleaching wood-containing papers.

However, sulfinic derivatives are not generally stable in storage. It is therefore necessary to store them in a well-sealed container in a cool, dry place, but they still degrade during storage, a process which can, under unfavorable circumstances, lead to self-ignition of the stored goods; as a result, sulfinic derivatives may have to be classified as dangerous chemicals. Besides this, their degradation leads to a constant reduction of the content of sulfinic derivatives in the stored goods and causes an unpleasant odor of sulfur dioxide and/or hydrogen sulfide which, in dyeing processes for example, is transferred to the dyed fabrics and thus to the clothing manufactured therefrom. This odor can be masked by perfuming, but this requires extra processing and does not solve the basic problem or other problems associated with poor stability in storage, such as the continual drop in the value of the stored goods, since a diminishing content of sulfinic derivative in the composition means that more and more of the composition will be required to achieve the same end. Another drawback associated with this poor stability in storage is the resultant inclination of the product to become sticky, which impairs its handling properties, for example its flow characteristics when it is removed from bins or its conveyability in screw transporters. The stability in storage of the sodium salts of sulfinic acid mostly used commercially is poorer than that of zinc salts of sulfinic acid, which are seldom used and which are not suitable for every application on account of the toxicity of zinc ions to aquatic organisms.

Sulfinic derivatives are therefore traded and used usually in the form of compositions in which the sulfinic derivatives are stabilized to counteract degradation by the addition of stabilizing agents. Thus JP-A 1970/26,610 (Derwent Abstract No 61104R-E), for example, teaches the admixture of from 1 to 50 parts of anhydrous sodium hydrogensulfite to 100 parts of sodium dithionite. JP-A 51,110,497 (Derwent Abstract No 85930X/46) discloses stabilized dithionite compositions which contain alkali metal carbonate and alkali metal bicarbonate or alkali metal benzoate. DE-A 2,031,820 discloses the stabilization of solid sodium dithionite particles by the application of coatings of propoxylated cellulose or starch. U.S. Pat. No. 3,054,658 teaches the stabilization of sodium dithionite by admixture with a sodium or potassium salt of a $C_1$–$C_{10}$ fatty acid or benzoic acid. DE-A 2,107,959 teaches the stabilization of sodium dithionite by admixture with calcined soda and sodium diethylenetriamine pentaacetate. U.S. Pat. No. 5,296,210 discloses the stabilization of sodium dithionite by means of oxidic hygroscopic compounds or mixtures of compounds having alkaline properties. Explicitly mentioned are CaO, BaO, $CaSO_4$/$Na_2CO_3$, $SiO_2$/$Na_2CO_3$, $Al_2O_3$/$Na_2CO_3$ and CaO/BaO. However, these substances suffer from the drawback of being insoluble in conventional ready-made, particularly aqueous, solutions of sulfinic derivatives, which hampers handling and use thereof on an industrial scale. German patent application No. 19905395.2 (filing date Oct. 2, 1999) discloses compositions which contain at least one sulfinic derivative and magnesium sulphate. These compositions show substantially slower degradation of the sulfinic derivative and considerably improved olfactory properties but experience shows that in some applications they can give rise to undesirable or even troublesome turbidity or precipitation in the solutions commonly used therein.

It is thus an object of the invention to provide a further composition containing sulfinic derivatives in which the sulfinic derivatives are stabilized to degradation to a higher degree than in most known compositions and, in addition, the occurrence of turbidity or precipitation during use of this composition is minimized.

Accordingly, we have found a composition which contains at least one sulfinic derivative and potassium carbonate. The composition of the invention shows a distinct improvement in stability over known compositions, in particular less reduction of the content of sulfinic derivative and less generation of objectionable odors and reduces the occurrence of turbidity or precipitation in solutions containing this composition.

The composition of the invention is preferably a solid composition and more preferably a solid flowable composition, from which the commercial solutions of sulfinic derivative(s) are prepared, for example by dissolution in a solvent such as water.

The composition of the invention contains at least one sulfinic derivative, which can be any known sulfinic derivative.

Sulfinic derivatives conform to the general formula

R—S(O)—O$^-$M$^+$.

The substituent R denotes an organic radical, such as a substituted or unsubstituted alkyl or aryl radical, or an inorganic radical, such as a substituted or unsubstituted sulfino or sulfinato radical.

Suitable alkyls are straight-chain or branched $C_1$–$C_{10}$ alkyl groups which may be substituted. Preference is given to the use of $C_1$–$C_4$ alkyls such as methyl, ethyl, n-propyl, isopropyl, n-butyl, sec-butyl, isobutyl or tert-butyl and more preferably to the use of a methyl group. Substituents other than hydrogen substituents can be used in these radicals, for example halogens such as fluorine, chlorine, bromine or iodine, oxygen-containing substituents such as oxy, alkoxy and/or hydroxy radicals, and/or nitrogen-contain-ing substituents such as amino and/or imino radicals. Preferably hydroxy or amino and imino radicals are used. Particularly preferred is the use of a 1-hydroxyalkyl radical, in particular a 1-hydroxyethyl or 1-hydroxymethyl radical (R=$CH_3$—CH(OH)— or HO—$CH_2$—) or an amino/imino methyl radical (R=$H_2$N—(HN)C—) or condensation products of the hydroxyalkyl radicals with ammonia (R=$H_2$N—CHR'—, M$^{+-}$O—(O) S—CHR'—NH—CHR'— or [M$^{+-}$O—(O) S—CHR']$_2$N—CHR'—), where M$^+$ has the meaning defined below and R' stands for hydrogen or alkyl, particularly methyl. If $M^+$ and $R'$ occur more than once in a compound they can denote different substituents.

Suitable aryls are aromatic radicals containing at least 6 carbon atoms, which may be substituted. Preference is given to the use of substituted or unsubstituted phenyl groups. Substituents other than hydrogen can be used in these radicals, for example halogens such as fluorine, chlorine, bromine or iodine, oxygen-containing substituents such as alkoxy and/or hydroxy radicals and/or nitrogen-containing substituents such as (alkyl)amino radicals.

Suitable inorganic radicals are all radicals which do not impair the stability of the sulfinic acid unit. Preference is given to the use of sulfur-containing radicals and more preferably to the use of a sulfino or sulfinato radical ($R=X^{+-}O—(O)S—$).

The substituent $M^+$ of the sulfinic derivatives is a cation, for example a proton, a unipositively charged metal cation or an equivalent multipositively charged metal cation as required to compensate the electric charges.

The unipositively charged cation can be for example a cation of an alkali metal such as lithium, sodium, potassium, rubidium or cesium, of which sodium and potassium are preferred, sodium being particularly preferred. The multipositively charged cation used can be for example a cation of an alkaline-earth metal such as magnesium, calcium, strontium or barium or some other divalent metal such as zinc, of which magnesium, calcium and zinc are preferred, zinc being particularly preferred. Alternatively, mixtures of unipositively and multipositively charged cations can be used, provided overall charge neutrality is achieved.

In a preferred embodiment, the composition of the invention contains at least one sulfinic derivative selected from the following group:

zinc dithionite $ZnS_2O_4$, sodium dithionite $Na_2S_2O_4$, zinc 1-hydroxyethanesulfinate $(H_3C—CH(OH)—SO_2)_2Zn$, sodium 1-hydroxyethanesulfinate $H_3C—CH(OH)—SO_2Na$, zinc 1-aminoethanesulfinate $(H_3C—CH(NH_2)—SO_2)_2Zn$, sodium 1-aminoethanesulfinate $H_3C—CH(NH_2)—SO_2Na$, zinc 1-iminoethanesulfinate $HN[—CH(CH_3)—SO_2]_2Zn$, sodium 1-iminoethanesulfinate $HN[—CH(CH_3—SO_2Na]_2$, zinc 1-nitriloethanesulfinate $[N[—CH(CH_3)—SO_2]_3]_2Zn_3$, sodium 1-nitriloethanesulfinate $N[—CH(CH_3)—SO_2Na]_3$, zinc hydroxymethanesulfinate $(H_2C(OH)—SO_2)_2Zn$, sodium hydroxymethanesulfinate $H_2C(OH)—SO_2Na$, zinc aminomethanesulfinate $(H_2C(NH_2)—SO_2)_2Zn$, sodium aminomethanesulfinate $H_2C(NH_2)—SO_2Na$, zinc iminomethanesulfinate $HN[—CH_2—SO_2]_2Zn$, sodium iminomethanesulfinate $HN[—CH_2—SO_2Na]_2$, zinc nitrilomethanesulfinate $[N[—CH_2—SO_2]_3]_2Zn_3$, sodium nitrilomethanesulfinate $N[—CH_2—SO_2Na]_3$ and aminoiminomethanesulfinic acid $H_2N—(HNC—SO_2H$.

In a particularly preferred embodiment it contains zinc dithionite and/or sodium dithionite, very preferably sodium dithionite. Dithionites ($R=M^{+-}O—(O)S—$), frequently referred to as hypodisulfites or hydrosulfites, are usually prepared by reduction of sulfurous acid or hydrogen sulfite using strong reducing agents. On an industrial scale this reduction is mostly effected using zinc dust, sodium amalgam or sodium formate as reducing agents, in which case zinc dithionite or sodium dithionite is formed respectively. The commercial dithionites produced by these various processes are frequently designated "zinc dust goods", "amalgam goods" or "formate goods" respectively. Hydroxmethylsulfinates ($R=HO—CH_2—$) are usually prepared by reduction of the corresponding sulfonyl chloride $R—SO_2Cl$ using zinc dust, sodium amalgam or sodium formate as reducing agents, in which case the corresponding zinc or sodium salt is formed. These products are caused to react with ammonia to give the corresponding amino, imino or nitrilo compounds. Aminoiminomethanesulfinic acid ($R=H_2N(HN)C—$, $M^+=H^+$), also referred to as formamidinosulfinic acid or thiourea dioxide, since it predominantly exists in the tautomeric form $O_2S=C(NH_2)_2$ in the solid state, is usually prepared by oxidation of thiourea with hydrogen peroxide.

An essential difference between the reduction of the appropriate parent compound by means of formates and the other commonly used processes for the preparation of sulfinic derivatives is that precipitation is carried out at acid pH's. In a preferred embodiment of the invention, the composition contains at least one sulfinic derivative which has been prepared by reduction of the parent compound in the acid range of pH's, in particular by reduction using a formate, especially sodium formate, as reducing agent.

Commercial sulfinic derivatives are not usually in a pure state but contain a certain amount of minor constituents, for example unconverted parent compounds, by-products of the reduction, degradation products of the sulfinic derivatives and/or auxiliary substances added during production thereof, such as sodium carbonate or hexamethylenetetramine. The content of such minor constituents is generally between approximately 5 wt % and 20 wt %, based on the total weight of the commercial product.

The composition of the invention also contains potassium carbonate. In a preferred embodiment it contains anhydrous potassium carbonate.

The content of sulfinic derivatives and potassium carbonate in such a freshly prepared composition can be varied virtually arbitrarily, but routine tests must be carried out in individual cases to find a compromise between an economically desirable high content of sulfinic derivatives and a sufficiently high content of potassium carbonate to give the required stability in storage.

The composition of the invention can comprise at least one sulfinic derivative, such as zinc dithionite, sodium dithionite, zinc hydroxymethanesulfinate, sodium hydroxymethanesulfinate, their condensation products with ammonia, and/or aminoiminomethanesulfinic acid, and potassium carbonate. In this case the freshly prepared composition generally contains potassium carbonate in an amount ranging from 0.1 to 15 wt %, preferably from 0.5 to 5 wt % and more preferably from 1 to 3 wt %. In the most preferred embodiment, the content of potassium carbonate is set at less than 2 wt %, for example at 1 wt %. These percentages are based in each case on the weight of the total composition and are calculated on the basis of anhydrous potassium carbonate.

The composition of the invention may contain, in addition to the sulfinic derivative(s) and potassium carbonate, any other desired constituents. Thus it may contain, in particular, not only the by-products usually formed during industrial preparation of sulfinic derivatives or unconverted starting materials, but also conventional stabilizing agents for sulfinic derivatives and/or any other known additives for commercial formulations containing sulfinic derivatives. It can contain for example additional auxiliaries such as activators, complexing agents such as nitrilotriacetic salts and/or ethylenediamine-tetraacetic salts, optical brighteners, bleaching agents, perfumes and/or surface-active agents such as surfactants and/or dispersing agents. Examples of such additional constituents of the composition of the invention are alkali metal salts such as the carbonate, hydrogencarbonate, sulfite, hydrogensulfite, disulfite, sulfate, mono-, di-, tri- and/or poly-phosphate, phosphonate, and/or carboxylate of sodium and/or potassium, surfactants and carbohydrates such as starch and cellulose and/or sugars such as glucose, fructose, maltose or saccharase, which may be alkoxylated. For each particular application, routine tests may be carried out to determine whether such additional constituents, in particular said metal salts, should be added or not and, if so, what quantity thereof is required for optimum results. Additional constituents which cause turbidity or precipitation in the quantity added and also any components which are unnecessary for achieving the desired technological effect are added either not at all or only in minor quantities. In a preferred embodiment, the composition contains no magnesium sulfate, no carbonates other than potassium carbonate and sodium carbonate and preferably no sodium carbonate, and/or no bicarbonates. Furthermore, the composition preferably contains sugars and/or complexing agents. If added, sugars and/or complexing agents are present in a quantity of generally at least 0.2 wt %, preferably at least 1 wt % and more preferably at least 2 wt % and not more than 20 wt %, preferably not more than 15 wt % and more preferably not more than 10 wt %, based in each case on the total composition.

Generally such a freshly prepared composition of the invention contains a total of from 15 to 90 wt %, preferably from 30 to 85 wt % and more preferably from 40 to 80 wt % of sulfinic derivative(s) based, in each case, on the total composition. Its content of potassium carbonate, calculated as anhydrous potassium carbonate, is generally at least 0.01 wt %, preferably at least 0.2 wt % and more preferably at least 0.5 wt % and generally not more than 10 wt %, preferably not more than 5 wt % and more preferably not more than 3 wt %, based in each case on the total composition, the other constituents of the composition of the invention supplementing the amounts of sulfinic derivatives and potassium carbonate to make up to 100 wt %.

The composition of the invention is prepared by adding potassium carbonate during or after the preparation of the sulfinic derivative(s) or commercial formulations thereof. The method or time of addition of the potassium carbonate is not generally of crucial importance and such addition can be carried out in any known manner. For example solid potassium carbonate or a potassium carbonate-containing solution or suspension in a suitable solvent or suspending agent or a mixture of such solvents or suspending agents can be added to the reaction mixture used for the preparation of a sulfinic derivative or at any stage of said process. Suitable solvents or suspending agents are for example water, ethers such as diethyl ether, di-n-propyl ether, diisopropyl ether, di-n-butyl ether, methyl-tert-butyl ether, ethyl-tert-bu-tyl ether and/or hydrocarbons such as pentane, hexane, benzene, toluene, or xylene.

Instead of potassium carbonate itself, there can be added other substances which give potassium carbonate in the final composition. Thus there may be added potassium salts other than potassium carbonate and sources of carbonate ions, for example potassium halides such as potassium chloride and/or bromide, potassium sulfate, potassium nitrate, potassium sulfite, alkali metal carbonates such as sodium carbonate and/or ammonium carbonate.

Preferably solid potassium carbonate or, in a particularly preferred embodiment, anhydrous solid potassium carbonate is mixed in during the conventional blending process for the preparation of commercial compositions of sulfinic derivatives, in which process commercial sulfinic derivative (s) are blended with known additives. The potassium carbonate is added in the particle sizes conventionally used for solid additives for such compositions and the particle size of the potassium carbonate can be varied virtually unlimitedly within this range. When use is made of more finely divided potassium carbonate, a better stabilizing action is usually achieved, but handling of the product is hampered due to the increased amount of dust formed in the case of very finely divided material, so that in some circumstances it will be necessary to determine the best particle size of the potassium carbonate for use in a particular application. Generally the average particle size (equal to 50 wt % retention of the potassium carbonate on a sieve of the specified mesh size) is from 0.005 to 1.0 mm, usually from 0.02 to 0.5 mm.

The compositions of the invention can be stored for longer periods of time or at higher temperatures (for example in dye shops in tropical countries) than is the case with known compositions or show, when stored for comparatively long periods, less generation of objectionable odors, less reduction in the content of sulfinic derivative(s) and/or less inclination to self-ignition. Similarly, the composition of the invention is less sticky than the commercial compositions. For example, it can be readily metered by means of screw conveyors without sticking to the walls thereof. Furthermore the compositions of the invention do not cause turbidity or precipitation in most fields of application.

EXAMPLES

There were prepared 17 different sulfinic derivative formulations, the composition of which is given in Table 1. Their content of dithionite was determined iodometrically. Each of these compositions was stored at 50° C. for a week (Comparative Examples C1 to C17), after which the content of dithionite was again determined and the olfactory impression evaluated sensorily. The compositions of Comparative Examples 11 and 12 contained no dithionite, but instead sodium or zinc hydroxymethanesulfinate was used. Thus the determination of the dithionite content was omitted.

Alongside these comparative examples there were prepared 17 other compositions which differed from the comparative examples in that part of the dithionite or hydroxymethanesulfinate was replaced by potassium carbonate as listed in Table 2. These compositions were also stored at 50° C. for a week (experiments 1 to 17) after which the content of dithionite was determined (except in the dithionite-free compositions used in experiments 11 and 12) and the olfactory impression was evaluated sensorily.

Information on Tables 1 and 2:

Tables 1 and 2 give the stability and olfactory properties of the compositions containing sulfinic derivatives used in Comparative Examples C1 to C17 and Examples 1 to 17 of the invention.

All percentages are by weight, based on the total composition.

The trade names owned by BASF Aktiengesellschaft, Ludwigshafen, Germany used for some constituents denote commercial formulations of the following chemicals:

Rongalit®C sodium hydroxymethanesulfinate,
Decrolin® zinc hydroxymethanesulfinate,
Trilon®A nitrilotriacetic acid and the (sodium) salts thereof,
Trilon®B ethylenediaminetetraacetic acid and the (sodium) salts thereof.
Dequest® is a trade mark of the Monsanto Company, U.S.A., for the phosphonates. These are commonly used commercial products.

In the odor tests the following grading was used:
– – strongly objectionable, intolerable in industrial applications;
– objectionable, only tolerable in industrial applications with masking, for example by perfuming;
+ less objectionable, tolerable in industrial applications;
++ neutral, not objectionable.

RESULTS

In all cases there was a distinct improvement in the olfactory properties of the stored product comprising the compositions of the invention of Examples 1 to 17 compared with those of the compositions of the Comparative Examples C1 to C17, and in most cases there was a distinctly lower measurable reduction of the original dithionite content, particularly in cases where the composition of the corresponding comparative example shows a comparatively more rapid reduction of the dithionite content.

The addition of potassium carbonate to the known sulfinic derivative-containing compositions thus reduces the nasal nuisance and causes better stabilization of the sulfinic derivatives used and is thus a convenient and cheap method of stabilizing compositions containing sulfinic derivatives.

TABLE 1

| Comparative Example No. | C1 | C2 | C3 | C4 | C5 | C6 | C7 | C8 | C9 | C10 | C11 | C12 | C13 | C14 | C15 | C16 | C17 |
|---|---|---|---|---|---|---|---|---|---|---|---|---|---|---|---|---|---|
| hydrosulfite, formate goods | 100 | | | 70 | | | | 80 | | | | | 25 | | 70 | | 60 |
| hydrosulfite, zinc dust goods | | 100 | | | 70 | | | | | 50 | | | | 50 | | | |
| hydrosulfite, amalgam goods | | | 100 | | | 70 | 80 | | 70 | | | | 25 | | | 70 | |
| sodium carbonate | | | | 20 | | | | 10 | | | | | 50 | | | | |
| sodium bicarbonate | | | | | 20 | | | | | | | | | | 20 | | |
| sodium sulfite | | | | | | 20 | 5 | | | | | 15 | | 35 | | 20 | |
| sodium disulfite | | | | | | | | | | 40 | | | | 15 | | | |
| sodium sulfate | | | | | | | | | | 10 | | | | | | | 30 |
| glucose | | | | | | | 15 | | | | | | | | | | |
| Rongalit C | | | | | | | | | 10 | 10 | | 80 | | | | | |
| Decrolin | | | | | | | | | | | | | 75 | | | | |
| thiourea dioxide | | | | | | | | | | 10 | | | | | | | |
| Trilon A | | | | | | | | | | 10 | | 20 | 10 | | | 10 | |
| Trilon B | | | | | | | 10 | | | | | | | | | | 10 |
| Dequest 2060 S | | | | | 10 | | | | | | | | | | | | |
| sodium triphosphate | | | | 10 | | | | | | | | | | | | | |
| curd soap | | | | | | | | | | | | | | | 10 | | |
| Na dithionite content | 89 | 89 | 90 | 62 | 63 | 63 | 73 | 72 | 63 | 45 | | | 45 | 45 | 63 | 62 | 55 |
| Properties following storage for 1 week at 50° C.: | | | | | | | | | | | | | | | | | |
| odor | – | – | + | – | – | – | – – | – – | – – | – | – | – – | – | – | – – | – | – |
| Na dithionite content | 89 | 89 | 90 | 61 | 61 | 62 | 69 | 71 | 60 | 45 | | | 45 | 45 | 60 | 60 | 52 |

TABLE 2

| Example No. | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| hydrosulfite, formate goods | 99 | | | 68 | | | | 75 | | | | | 22 | | 67 | | 58 |
| hydrosulfite, zinc dust goods | | 99 | | | 68 | | | | | 48 | | | | 47 | | | |
| hydrosulfite, amalgam goods | | | 99 | | | 68 | 79 | | 68 | | | | 25 | | | 68 | |
| sodium carbonate | | | | 20 | | | | 10 | | | | | 50 | | | | |
| sodium bicarbonate | | | | | 20 | | | | | | | | | | 20 | | |
| sodium sulfite | | | | | | 20 | 5 | | | | | 15 | | 35 | | 20 | |
| sodium disulfite | | | | | | | | | | 40 | | | | 15 | | | |
| sodium sulfate | | | | | | | | | | 10 | | | | | | | 30 |
| glucose | | | | | | | 15 | | | | | | | | | | |
| Rongalit C | | | | | | | | | 10 | 10 | | 75 | | | | | |
| Decrolin | | | | | | | | | | | | | 72 | | | | |
| thiourea dioxide | | | | | | | | | | 10 | | | | | | | |
| Trilon A | | | | | | | | | | 10 | | 20 | 10 | | | 10 | |
| Trilon B | | | | | | | | 10 | | | | | | | | | 10 |
| Dequest 2060 S | | | | | | | | | 10 | | | | | | | | |
| sodium triphosphate | | | | | | | | 10 | | | | | | | | | |
| curd soap | | | | | | | | | | | | | | | 10 | | |

TABLE 2-continued

Examples illustrating the invention

| Example No. | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| potassium carbonate anhydrous | 1 | 1 | 1 | 2 | 2 | 2 | 1 | 5 | 2 | 2 | 5 | 3 | 3 | 3 | 3 | 2 | 2 |
| Na dithionite content | 89 | 90 | 89 | 62 | 61 | 61 | 70 | 68 | 61 | 43 | | | 42 | 41 | 61 | 61 | 52 |
| Properties following storage for 1 week at 50° C.: | | | | | | | | | | | | | | | | | |
| odor | ++ | ++ | ++ | + | ++ | + | + | − | − | + | ++ | + | ++ | + | + | ++ | ++ |
| Na dithionite content | 89 | 90 | 89 | 62 | 61 | 61 | 70 | 67 | 60 | 43 | | | 42 | 41 | 60 | 61 | 52 |

We claim:

1. A solid composition containing at least one sulfinic derivative and potassium carbonate.

2. A composition as defined in claim 1 containing at least one sulfinic derivative selected from the group consisting of zinc dithionite, sodium dithionite, zinc 1-hydroxyethanesulfinate, sodium 1-hydroxyethanesulfinate, zinc 1-aminoethanesulfinate, sodium 1-aminoethanesulfinate, zinc 1-iminoethanesulfinate, sodium 1-iminoethanesulfinate, zinc 1-nitriloethanesulfinate, sodium 1-nitriloethanesulfinate, zinc hydroxymethanesulfinate, sodium hydroxymethanesulfinate, zinc aminomethanesulfinate, sodium aminomethanesulfinate, zinc iminomethanesulfinate, sodium iminomethanesulfinate, zinc nitrilomethanesulfinate, sodium nitrilomethanesulfinate and aminoiminomethanesulfinic acid.

3. A composition as defined in claim 2 containing zinc dithionite and/or sodium dithionite.

4. A composition as defined in claim 3 containing sodium dithionite.

5. A composition as defined in claim 1 containing a total of from 15 to 90 wt % of sulfinic derivatives based on the total composition.

6. A composition as defined in claim 1 containing from 0.01 to 10 wt % of potassium carbonate based on the total composition.

7. A composition as defined in claim 5 which contains from 0.01 to 10 wt % of potassium carbonate based on the total composition.

* * * * *